(12) United States Patent
Phillips et al.

(10) Patent No.: US 10,541,046 B2
(45) Date of Patent: Jan. 21, 2020

(54) CREATING GENETIC DEVICES

(75) Inventors: Andrew Nicholas John Brojer Phillips, Cambridge (GB); Michael David Pedersen, Edinburgh (GB)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1012 days.

(21) Appl. No.: 12/552,829

(22) Filed: Sep. 2, 2009

(65) Prior Publication Data

US 2011/0054654 A1    Mar. 3, 2011

(51) Int. Cl.
*G16B 50/00* (2019.01)
*G06F 17/50* (2006.01)
*G16B 5/00* (2019.01)
*G16B 20/00* (2019.01)

(52) U.S. Cl.
CPC .......... *G16B 50/00* (2019.02); *G06F 17/504* (2013.01); *G16B 5/00* (2019.02); *G16B 20/00* (2019.02)

(58) Field of Classification Search
None
See application file for complete search history.

(56) References Cited

U.S. PATENT DOCUMENTS

| | | | | |
|---|---|---|---|---|
| 4,922,432 | A * | 5/1990 | Kobayashi et al. | 716/102 |
| 5,197,016 | A * | 3/1993 | Sugimoto et al. | 716/55 |
| 5,703,789 | A * | 12/1997 | Beausang et al. | 716/103 |
| 7,225,423 | B2 * | 5/2007 | Bhattacharya et al. | 716/102 |
| 2002/0142454 | A1 * | 10/2002 | Cracauer | B01J 19/0046 435/287.2 |
| 2008/0096771 | A1 * | 4/2008 | Hubbell | B01J 19/0046 506/13 |
| 2008/0177054 | A1 * | 7/2008 | Evans | B01J 19/0046 536/25.31 |
| 2009/0023605 | A1 * | 1/2009 | Lebl | B01J 19/0046 506/27 |
| 2009/0148353 | A1 * | 6/2009 | Downing | B01J 19/0046 422/131 |

OTHER PUBLICATIONS

Canton, B., Labno, A. & Endy, D. Refinement and standardization of synthetic biological parts and devices. Nature Biotechnology 26, 787-793 (2008).*
Beckmann, R., Bieker, U. & Markhof, I. Application of constraint logic programming for VLSI CAD tools. Constraints in Computational Logics 845, 183-200 (1994).*
Chin, J.W. Modular approaches to expanding the functions of living matter. Nature Chemical Biology 2, 304-311 (2006).*
Skerker, J.M. et al. Rewiring the specificity of two-component signal transduction systems. Cell 133, 1043-1054 (2008).*
Glick, B. R. Metabolic load and heterologous gene expression. Biotechnol. Adv. 13, 247-261 (1995).*
Afif et al., "The ratio between ccda and ccdb modulates the transcriptional repression of the ccd poison-antidote system", 2001 Blackwell Science Ltd, Molecular Microbiology, pp. 73-82.
Andrianantoandro et al., "Synthetic biology: new engineering rules for an emerging discipline", Molecular Systems Biology, 2006, EMBO and Nature Publishing Group, pp. 1-14.
Apt et al., "Constraint logic programming using ECLiPSe", Cambridge University Press, 2007, 40 pages.
Balagadde et al. , "A synthetic *Escherichia coli* predator-prey ecosystem", Molecular Systems Biology 4, Article No. 187, 2008, EMBO and Nature Publishing Group, 8 pages.
Bergmann et al., "SBW—a modular framework for systems biology", Proceedings of the 2006 Winter Simulation Conference, 9 pages.
Blossey et al., "Compositionality, stochasticity and cooperativity in dynamic models of gene regulation", HFSP Journal, HFSP Publishing, vol. 2, No. 1, Feb. 2008, pp. 17-28.
Bornstein et al., "LibSBML: an API library for SBML", Bioinformatics Applications Note, vol. 24, No. 6, Published by Oxford University Press, 2008, pp. 880-881.
Buchler et al., "On schemes of combinatorial transcription logic", PNAS, vol. 100, No. 9, Apr. 2003, 6 pages.
Cai et al., "A syntactic model to design and verify synthetic genetic constructs derived from standard biological parts", Bioinformatics, Bol. 23, No. 20, 2007, pp. 2760-2767.
Chabrier-Rivier, et al., "The biochemical abstract machine BIOCHAM", CMSB 2004, LNBI 3082, Springer-Verlag Berlin Heidelberg, 2005, pp. 172-191.
Ciocchetta et al., "Bio-PEPA: an extension of the process algebra PEPA for biochemical networks", From Biology to Concurrency and Back (FBTC), 2007, 15 pages.
Cox et al., "Programming gene expression with combinatorial promoters", Molecular Systems Biology 3, Article 145, 2007, EMBO and Nature Publishing Group, 11 pages.
Danos et al., "Rule-based modelling of cellular signalling", Springer-Verlag Berlin Hiedelberg, 2007, 25 pages.

(Continued)

*Primary Examiner* — Soren Harward
(74) *Attorney, Agent, or Firm* — Drinker Biddle & Reath LLP

(57) ABSTRACT

Creating genetic devices for use in micro-organisms or other biological systems is described. In an embodiment a computer system receives at a program editor, input specifying a plurality of part designs, at least some of which comprise part properties expressed as logical variables; and the input also specifies constraints on the logical variables. For example, the input is a computer program which specifies constraints on the logical variables which, for example, relate to properties of the DNA sequences such as reactions and biological behaviors. In an example, a compiler resolves the constraints using a database of genetic parts in order to generate candidate parts for the proposed genetic device. In examples the sequences of genetic parts are translated into reactions and simulated using an automated simulator and/or implemented in a living cell or other biological system. In embodiments the compiler also uses a database of reactions.

17 Claims, 17 Drawing Sheets

(56) References Cited

OTHER PUBLICATIONS

Elowitz et al., "A synthetic oscillatory network of transcriptional regulators", Nature, vol. 403, Jan. 2000, 4 pages.
Endy, "Foundations for engineering biology", Nature Publishing Group, vol. 238, Nov. 2005, 5 pages.
Fisher et al., "Executable cell biology", Nature Biotechnology, vol. 25, Nov. 2007, pp. 1239-1249.
Garfinkel, "A machine-independent language for the simulation of complex chemical biochemical systems", Computers and Biomedical Research, Apr. 1968, 14 pages.
Hermsen et al., "Transcriptional regulation by competing transcription factor modules", PLoS Computational Biology, vol. 2, Issue 12, Dec. 2006, pp. 1552-1560.
Hucka et al., "The systems biology markup language (SBML): a medium for representation and exchange of biochemical network models", Bioinformatics, vol. 19, No. 4, Publised by Oxford University Press 2003, pp. 524-531.
Mallavarapu et al., "Programming with models: modularity and abstraction provide powerful capabilities for systems biology", Journal of the Royal Society Interface, Feb. 2008, pp. 1-15.
Marchisio et al., "Computational design of synthetic gene circuits with composable parts", Bioinformatics. vol. 24, No. 17, published by Oxford University Press, 2008, pp. 1903-1910.
Marguet et al, "Biology by design: reduction and synthesis of cellular components and behaviour", The Journal of the Royal Society Interface published on-line at rsif.royalsocietypublishing.org, Jan. 2007, 18 pages.
Pedersen et al., "A language for biochemical systems", retrieved from the internet at http://homepages.inf.ed.ac.uk/s0677975/papers/lbs-cmsb-short.pdf on Dec. 1, 2009, 21 pages.
Pedersen et al, "Towards programming languages for genetic engineering of living cells", Journal of the Royal Society Interface published on-line Apr. 15, 2009 at rsif.royalsocietypublishing.org, 15 pages.
Regev et al., "Representation and simulation of biochemical processes using the pi-calculus process algebra", Proceedings of the Pacific Symposium of Biocomputing, 2001, 12 pages.
Sauro et al., "Jarnac: a system for interactive metabolic analysis", Retreived from the internet: http://sbw.kgi.edu/sbwWiki/_media/sysbio/papers/jarnac_-_a_system_for_interactive_metabolic_analysis.pdf on Dec. 1, 2009, pp. 221-228.
Shrager et al., "Deductive biocomputing", PLoS One, Apr. 2007, Issue 1, 9 pages.

\* cited by examiner luxR + m3OC6HSL → {1.0} luxR-m3OC6HSL luxR-m3OC6HSL → {1.0} luxR+m3OC6HSL lasR+m3OC12HSL → {1.0} larR-m3OC12HSL lasR-m3OC12HSL → {1.0} lasR+m3OC12HSL luxI ~ → {1.0}m3OC6HSL lasI ~ → {1.0}m3OC12HSL ccdA ~ ccdB → {1.0} ccdA2 ~ ccdB → {0.00001} m3OC6HSL → {1.0} [m3OC6HSL]

m3OC12HSL → {1.0} [m3OC12HSL]

[m3OC6HSL] → {1.0} m3OC6HSL

[m3OC12HSL] → {1.0} m3OC12HSL

FIG. 2

| Type | ID | Properties |
| --- | --- | --- |
| pcr | c0051 | codes(cIR, 0.001) |
| pcr | c0040 | codes(tetR, 0.001) |
| pcr | c0080 | codes(araC, 0.001) |
| pcr | c0012 | codes(lacI, 0.001) |
| pcr | c0061 | codes(luxI, 0.001) |
| pcr | c0062 | codes(luxR, 0.001) |
| pcr | c0079 | codes(lasR, 0.001) |
| pcr | c0078 | codes(lasI, 0.001) |
| pcr | cunknown3 | codes(ccdB, 0.001) |
| pcr | cunknown4 | codes(ccdA, 0.1) |
| pcr | cunknown5 | codes(ccdA2, 10.0) |
| prom | r0051 | neg(cIR, 1.0, 0.5, 0.00005) con(0.12) |
| prom | r0040 | neg(tetR, 1.0, 0.5, 0.00005) con(0.09) |
| prom | i0500 | neg(araC, 1.0, 0.000001, 0.0001) con(0.1) |
| prom | r0011 | neg(lacI, 1.0, 0.5, 0.00005) con(0.1) pos(lasR-m3OC12HSL, 1.0, 0.8, 0.1) |
| prom | runknown2 | pos(luxR-m3OC6HSL, 1.0, 0.8, 0.1) con(0.000001) |
| rbs | b0034 | rate(0.1) |
| ter | b0015 | |

FIG. 3

| Part | Representation |
|---|---|
| X : prom |  |
| X : rbs |  |
| X : pcr |  |
| X : ter |  |

| Part Property & Reactions | Representation |
|---|---|
| X:prom<pos (P, RB, RUB, RTB)><br><br>g + P → {RB} g-P<br>g-P → {RUB} g + P<br>g-P → {RTB} g-P + m |  |
| X:prom<neg (P, RB, RUB, RTB)><br><br>g + P → {RB} g-P<br>g-P → {RUB} g + P<br>g-P → {RTB} g-P + m |  |
| X:prom<con(RT)><br>g → {RT} g + m<br>m → {rdm} |  |
| X:rbs<rate(R)><br>m →{R} m + P |  |
| X:pcr<codes(P, RD)><br>P → {RD} |  |

R0040: prom; b0034: rbs; c0040: pcr; b0015: ter

X1: prom<neg(tetR)>; X2: rbs;
X3: pcr<codes(tetR)>; X4: ter

X1: prom<neg(y)>; X2: RBS;
X3: pcr<codes(y)>; X4: ter prom<neg(y)>; rbs; pcr<codes(y)>; ter

| Reaction | Representation |
|---|---|
| C[S] → {RO} S |  |
| S → {RI} c[S] |  |
| E ~ S1 + ... + SN<br>→ {R} T1 + ... + TM |  | prom<neg(C)>; rbs; pcr<codes(A)>; ter;
prom<neg(A)>; rbs; pcr<codes(B)>; ter;
prom<neg(B)>; rbs; pcr<codes(C)>; ter

CREATING GENETIC DEVICES

BACKGROUND

Synthetic biology aims to design and create novel genetic devices to carry out some desired and well-defined function. For example, micro-organisms may be genetically engineered to improve crop yields, fight bacterial infections, detect pollutants, or convert sunlight into energy. Scientists typically begin with a list of requirements or desired functions of the genetic device to be created and then formulate suitable designs for the proposed device. The design and construction of a genetic device is a difficult task that is typically achieved through trial-and-error, which can be time-consuming and costly. In-silico models can help to improve the design process by allowing a range of designs to be simulated on a computer, before constructing the most promising ones in the lab, saving time and resources.

Some existing formal computer languages and frameworks have allowed the direct assembly of specific DNA sequences from a library of such sequences. However these approaches are limited as they require the scientist to exactly specify the DNA sequences to be used.

The embodiments described below are not limited to implementations which solve any or all of the disadvantages of known computer systems and software tools for creating and designing genetic devices.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Creating genetic devices for use in micro-organisms or other biological systems is described. In an embodiment a computer system receives at a program editor, input specifying a plurality of part designs, at least some of which comprise part properties expressed as logical variables; and the input also specifies constraints on the logical variables. For example, the input is a computer program which specifies constraints on the logical variables which, for example, relate to properties of the DNA sequences such as reactions and biological behaviors. In an example, a compiler resolves the constraints using a database of genetic parts in order to generate candidate parts for the proposed genetic device. In examples the sequences of genetic parts are translated into reactions and simulated using an automated simulator and/or implemented in a living cell or other biological system. In embodiments the compiler also uses a database of reactions.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein:

FIG. 2 is an example of part of a database of reactions associated with DNA sequences;

FIG. 3 is an example of part of a database of DNA sequences;

Like reference numerals are used to designate like parts in the accompanying drawings.

DETAILED DESCRIPTION

The detailed description provided below in connection with the appended drawings is intended as a description of the present examples and is not intended to represent the only forms in which the present examples may be constructed or utilized. The description sets forth the functions of the examples and the sequence of steps for constructing and operating the examples. However, the same or equivalent functions and sequences may be accomplished by different examples.

Although the present examples are described and illustrated herein as being implemented in a computer-based genetic device creation system, the system described is provided as an example and not a limitation. As those skilled in the art will appreciate, the present examples are suitable for application in a variety of different types of synthetic biology systems.

The term "part" is used to refer to a specific DNA sequence to be used in a living cell or other biological entity.

The term "part design" is used to refer to requirements that a desired part should meet. For example, a part design may be a part name identifying a specific desired part. A part design may also be a type of a desired part together with a set of properties describing the desired part, where the properties are expressed in terms of at least one logical variable. A non-exhaustive list of examples of part types is: ribosome binding site, promoter, protein coding region. A property of a part may also denote a type of that part. Other examples of part properties are given later in this document.

The term "device" is used to refer to at least one sequence of parts each sequence comprising at least one part.

The term "part template" is used to refer to a part name identifying a specific part, or to a logical variable representing an undetermined part.

The term "device template" is used to refer to one or more sequences of part templates, expressed in terms of one or more logical variables.

The term "reaction template" is used to refer to a set of chemical reactions expressed in terms of one or more logical variables.

The term "substitution" is used to refer to a mapping from logical variables to part or molecule names. A substitution can be applied to a device template or a reaction template in order to obtain a final device or set of reactions, respectively.

The term "species" is used to refer to a molecule that is a component of a chemical reaction, such as a reactant or product. A non-exhaustive list of examples is: mRNA, protein, complex of proteins, promoter.

Figure 1:
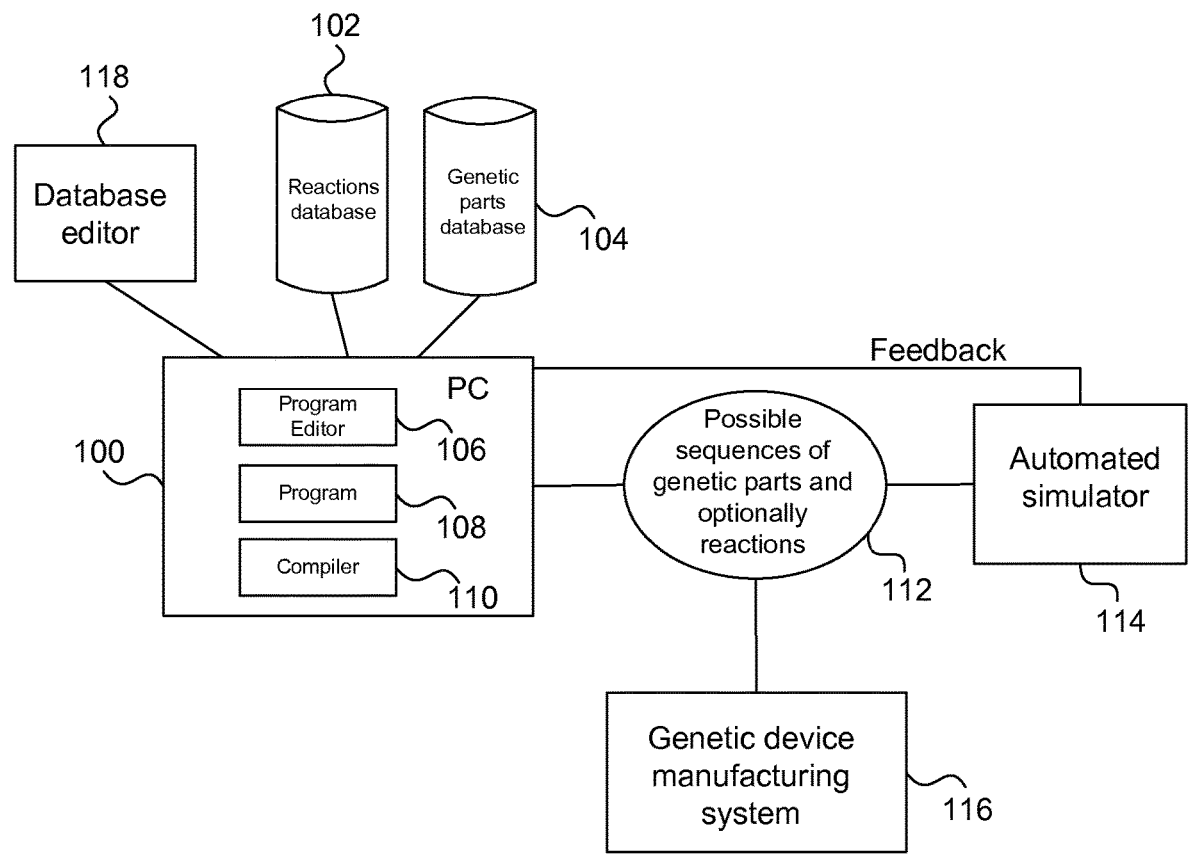
FIG. 1 is a schematic diagram of a system for creating a genetic device.

FIG. 1 is a schematic diagram of a system for creating a genetic device. The system comprises a computing based device 100 arranged to communicate with a reactions database 102 and a genetic parts database 104. The reactions database and the genetic parts database may be integral or independent of one another as illustrated. In some embodiments the databases 104, 102 may be provided at the computing based device itself. A processor of the computing based device 100 is arranged to execute a program editor 106 in which programs 108 can be constructed and edited and a compiler 110 which compiles and executes the programs 108. An output 112 of the computing based device 100 comprises a plurality of possible devices and optionally reactions. For example, a programmer may use the program editor 106 to form a computer program to create a device with particular requirements. For example, the requirements may relate to biological behaviors that a proposed micro-organism should have. The requirements are specified using constraints and these may be high-level or general so that the system may produce more than one possible device 112. Once a device 112 is produced by the system this may be realized using a genetic device manufacturing system 116. For example, to create a set of DNA sequences for insertion into a living cell, micro-organism or other biological system.

An automated simulator 114 may also be provided which may be computer-based for example. The automated simulator 114 may be integral with the computing based device 100 or may be independent. More detail about the automated simulator is given below with reference to FIG. 5.

A database editor 118 can be used to edit the content of the reactions database 102 and genetic parts database 104.

FIG. 2 is an example of part of a database of reactions associated with DNA sequences. The reactions database 102 comprises a plurality of reactions involving species, a non limiting list of examples is; basic reactions, enzymatic reactions and transport reactions. In this example the reactions are explicitly represented at the level of proteins and small molecules. For example, the reactions database represents reactions in the general form;

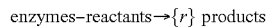

enzymes–reactants→{r} products where {r} is a specified mass action rate constant.

FIG. 3 is an example of part of a genetic parts database 104. As illustrated the genetic parts database 104 may comprise three columns, the first representing part types, the second representing unique IDs of DNA sequences, which may be taken from the Registry of Standard Biological Parts, and the third representing sets of properties. In the examples described herein the part types are: promoters prom, ribosome binding sites rbs, protein coding regions pcr and terminators ter. However, any suitable part types may be used and the examples given here are not intended to limit the invention.

Each genetic part in the database of parts 104 has one or more properties which relate at a high level to behaviors of that genetic part. Examples of properties are activation and inhibition by specific transcription factors, binding and unbinding rates, interaction with specific proteins, rates of protein degradation and others. The properties described herein are examples only and other properties may be used. In the examples described herein promoters can have the following sets of properties: pos(P,RB,RUB,RTB) and neg (P,RB,RUB,RTB), resulting in positive or negative regulation respectively. The name P denotes a transcription factor (a protein or a protein complex). The names RB and RUB are the binding and unbinding rates of the transcription factor to the promoter and RTB is the rate of transcription in the bound state. Promoters can also have the property con(RT), where RT is the constitutive rate of transcription in the absence of transcription factors. Protein coding regions have the property codes(P,RD), indicating the protein P they code for together with a rate RD of protein degradation. Ribosome binding sites can have the property rate(R) representing a rate of translation of mRNA. The rate information associated with the parts allows additional reactions at the level of gene expression to be deduced from part properties.

Using the program editor 106 a program 108 can be constructed using a programming language such as that described herein. An example of a suitable syntax and semantics for such a programming language is described later in this document. The program input to the program editor 106 may comprise a plurality of part sequences, modules, compartments and constraints together with localized variables. Parameterized modules can be used to add further levels of abstraction to the program 108 by attributing a module name to a portion of the program and enclosing a list of formal parameters, which can be referred to within the body of the module. In a non-limiting list of examples modules can act as positive gates, where a promoter is positively regulated by an input protein; can act as negative gates, where a promoter is negatively regulated by a protein; or can constitutively express a protein. Modules are described by the module keyword followed by the name of the module, a list of formal parameters and the body of the module enclosed in brackets { }. They can be invoked by naming them within the program together with a list of parameters.

The program may comprise compartments. Compartments can be used to represent the biological location of parts, such as a particular cell type in order to prevent unwanted cross talk between parts in cases where there may be a plurality of genetic devices implemented. The compartments may for example be biological compartments (e.g. a cell or a cell nucleus), physical compartments (e.g. different wells in a tray) and/or logical compartments (e.g. where there is known independence of parts).

In addition the programming language used to form the program may allow reactions to be represented as additional constraints on parts.

More detail of an example syntax for the programming language is now given.

Fixed sets of primitive species names $N_s$, part identifiers $N_p$ and variables $X$ are used. $x \in X$ represents variables, $n \in N_p$ represents part identifiers and $u \in U$ represents species, parts and variables, where $U \stackrel{\Delta}{=} N_s \cup N_p \cup X$. A type system may be provided to ensure, context-dependent use of u. The set of complex species is given by the set $S$ of multisets over $N_s \cup X$ and is ranged over by $S$; multisets (i.e. sets which may contain multiple copies of each element) may be used in order to allow for homomultimers.

A fixed set T of part types t is provided together with a set $Q^t$ of possible part properties for each type $t \in T$.

$$Q \triangleq \bigcup_{t \in T} Q^t$$

is defined and $Q^t \ddot{O} Q^t$ ranges over finite sets of properties of type t. Functions $FV: Q \mapsto X$ and $FS: Q \mapsto S$ are given for obtaining the variables and species of properties, respectively. These functions are extended to other program constructs as required.

c ranges over a given set of compartments, p ranges over a given set of program (module) identifiers, m ranges over the natural numbers —$\mathbb{N}$, r ranges over $\mathbb{R} \cup X$ and $\otimes$ ranges over an appropriate set of arithmetic operators.

In an example, the tilde symbol (~) in a program grammar is used to denote lists, and the sum ($\Sigma$) formally represents multisets. A non limiting list of examples of a syntax for the programming language is given by the grammar listed below:

P::=u:t($Q^t$) Part u of type t with properties $Q^t$
:0 Empty program
:p(ũ){$P_1$};$P_2$ Definition of module p with formals ũ
:p(Ã) Invocation of module p with actuals Ã
:P|C Constraint C associated to program P
:$P_1$||$P_2$ Parallel composition of $P_1$ and $P_2$
:$P_1$;$P_2$ Sequential composition of $P_1$ and $P_2$
:c[P] Compartment c containing program P
:new x.P Local variable x inside program P
C::=R Reaction
  :T Transport reaction
  :K Numerical constraint
  :$C_1$|$C_2$ Conjunction of $C_1$ and $C_1$
R::=S~$\Sigma m_i \cdot S_i \rightarrow^r \Sigma m_j \cdot S_j$ Reactants $S_i$, products $S_j$
T::=S$\rightarrow^r$c[S] Transport of S into compartment c
  :c[S]$\rightarrow^r$S Transport of S out of compartment c
K::=$E_1$>$E_2$ Expression $E_1$ greater than $E_2$
E::=r Real number or variable
  :$E_1 \otimes E_2$ Arithmetic operation $\otimes$ on $E_1$ and $E_2$
A::=r Real number or variable
  :S Species Some language constructs are not represented explicitly in the grammar but are defined in terms of the syntax set out above. For example, reversible reactions are defined as the composition of two reactions, each representing one of two directions. The underscore (_) is used as a wild card to mean that any name can be used in its place. This wild card can be encoded using variables and the new operator; for example _:t($Q^t$)$\triangleq$ new x(x:t($Q^t$)). In the specific case of basic part programs the wild card can be omitted, i.e. t($Q^t$)$\triangleq$_:t($Q^t$). Constraints may be composed to the left of programs and the following definition may be used C|P$\triangleq$ P|C.

The program 108 can be compiled using the compiler 110. The compiler comprises two components; a parser and a corresponding translator which follows denotational semantics such as those described in more detail below. The translator invokes a prolog engine (or other suitable constraint resolution engine) for solving the input constraints. In order that the prolog engine can solve the input constraints, these may first be translated into prolog constraints by the translator. The translator can also generate reactions by directly taking the reactions contained in programs after substituting formal for actual parameters and by extracting reactions for the relevant parts. A translation to parts using the compiler is described in more detail with regard to FIG. 4 below.

The compiler 110 can optionally be used to translate the returned device into a set of associated reactions which can be simulated using the automated simulator 114. Feedback on the behavior of the sets of associated reactions provided by the automated simulator may be input to the program as additional constraints. For example, it may be used to narrow the constraints on reaction rates specified in the program to appropriate ranges for the desired behaviors. Once a device is found that, when simulated, displays the desired behavior it can be implemented in a living cell such as a bacterium using a genetic device manufacturing system 116. Alternatively the returned devices can be implemented without simulating the behavior on a trial and error basis.

By using the reactions and genetic parts databases in the manner described it is possible to readily capture the information needed to automatically translate models into DNA sequences which, when synthesized and put to work in living cells, express biological systems that satisfy the original requirements. Also, interactions between undetermined sequences of proteins and genes are taken into account. For example, the program may specify constraints and at that stage the actual sequences of DNA to be used are not known. The compiler is arranged to resolve the constraints in such a manner that interactions between possible DNA sequences are taken into account during the constraint resolution process.

Figure 4:
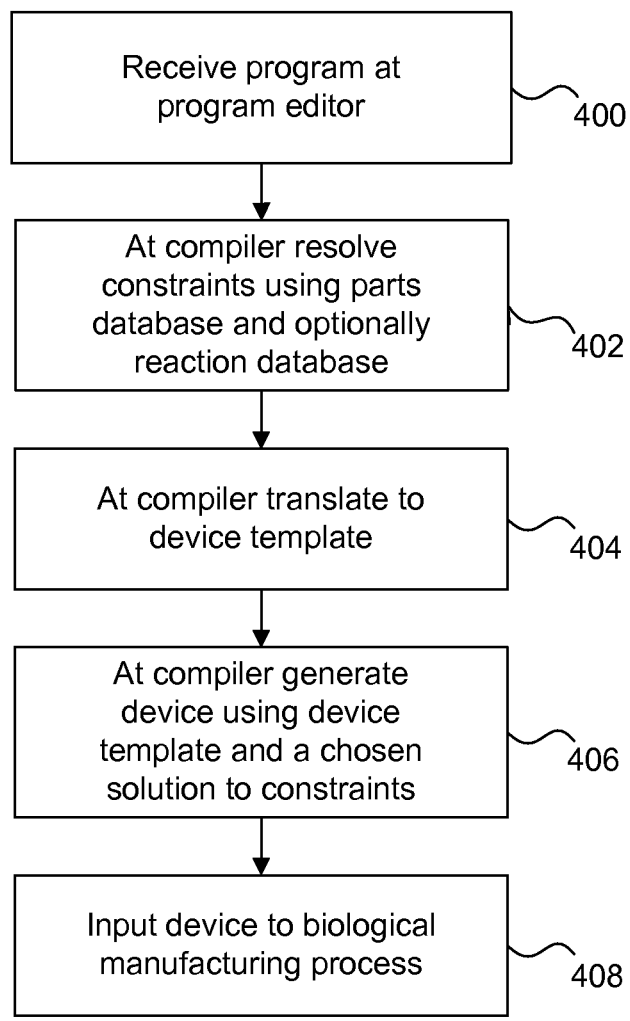
FIG. 4 is a flow diagram of a method of executing a program for a genetic circuit.

FIG. 4 is a flow diagram of a method at the computer-based device 100 of FIG. 1. A program is received 400 at a program editor. The program is compiled by resolving constraints 402 using the parts database; a device template is generated 404 and a chosen solution to the constraints is used to generate a device from the device template 406. The device may be used as input 408 to a biological manufacturing process.

The program received at the program editor may comprise a plurality of part designs, modules, compartments and constraints together with localized variables. The compiler 402 accesses the parts database and returns all the solutions to the constraints on part properties in the program. In addition acceptable ranges for rate properties can be specified in order to reduce the number of devices returned. For example constraints are specified using a constraint operator |. For example the binding rate RB can be constrained as; |0.9<RB|RB<1.1|

In an example, compilation 402 yields three structures. A device template, a reaction template (in the case that translation to reactions takes place) and a set of substitutions that map logical variables to part names and molecule names. The reaction template may be expressed as a Language for Biochemical systems (LBS) program. A Language for Biochemical Systems is discussed in detail in Pedersen and Plotkin, 2008 "A language for Biochemical systems. In M. Heiner A. M. Uhrmacher (Eds.), Proc. CMSB, Lecture Notes in Computer Science, Springer" which is incorporated herein by reference in its entirety. The reaction template provides the results of a translation in embodiments where this translation takes place.

The device template may be computed at the compiler in conjunction with the parts database 404 and optionally the reactions database 405. The device template is computed by in-lining module invocations, introducing fresh variables where part identifiers have been omitted and disregarding everything but the part identifiers/variables and their sequential/parallel compositions. The in-lining and introduction of variables yields an intermediate program. If parallel compositions are included, for example in a program with a plurality of compartments, then the device template consists of a list for each parallel program.

More detail about semantics of an example programming language used to form the program 108 is now given.

Transport reactions contain explicit compartment names which are important for simulation, but only the logical property that transport is possible is captured in the reaction database 405. The operator $(\cdot)^\downarrow$ on transport reactions is defined to ignore compartment names, where $(S \to c[S'])^\downarrow \stackrel{\Delta}{=} S \to [S']$ and $(c[S] \to S')^\downarrow \stackrel{\Delta}{=} [S] \to S'$. The meaning of a program is then given relative to global databases $K_b$ and $K_r$ of parts and reactions, respectively. These are assumed to be given by two finite sets of ground terms:

$$K_b \ddot{O} \{n{:}t(Q^t) | FV(Q^t) = \emptyset\}$$

and $K_r \ddot{O} \{R | FV(R) = \mathit{æ}\} \cup \{T^\downarrow | FV(T) = \emptyset\}$ Dom($\theta$) and Im($\theta$) are used to denote, respectively, the domain and image of a function $\theta$, $\emptyset$ is used to denote an empty set. CS is defined to be the set of context sensitive substitutions $(\theta, \rho, \sigma, \tau)$ where $\theta{:}X \to N_g \cup N_p \cup \mathbb{R}$ is a finite, partial function (the substitution).

$\rho \ddot{O} X$ is a set of variables over which $\theta$ is injective, i.e.

$$\cup x_1, x_2 \epsilon \rho(x_1 \neq x_2) \Rightarrow \theta(x_i) \neq \theta(x_2))$$

$\sigma, \tau \ddot{O} S$ are, respectively, the species names that have been used in the current context and the species names that are excluded for use, and $\sigma \Omega \tau = \emptyset$.

Context-sensitive substitutions represent solutions to constraints. They also capture the information necessary to ensure piece-wise injectivity over compartment boundaries, together with cross-talk avoidance.

The composition of two sets of context-sensitive substitutions is defined as follows:

$$\{(\theta_i, \rho_i, \sigma_i, \tau_i)\}_I \bigcirc \{(\theta'_j, \rho'_j, \sigma'_j, \tau'_j)\}_J \stackrel{\Delta}{=} \{(\theta_i \cup \theta'_j, \rho_i \cup \rho'_j, \sigma_i \cup \sigma'_j, \tau_i \cup \tau'_j)\}_{I \bowtie J} \cap CS$$

Informally, the composition consists of all possible pairwise unions of the operands which satisfy the conditions of context-sensitive substitutions. This means in particular that the resulting substitutions are functions, that they are infective over the relevant interval, and that they originate from pairs of context-sensitive substitutions for which the used names in one are disjoint from the excluded names in the other. So in practice, if two sets of context-sensitive substitutions represent the solutions to the constraints of two programs, their composition represents the solutions to the constraints of the composite program (e.g. the parallel or sequential compositions).

Each context-sensitive substitution in $\Theta$ satisfies the constraints given implicitly by a program and can be applied to the device template to obtain the final, concrete device. $\text{Dom}_s(\theta)$ is written for the subset of the domain of $\theta$ mapping to species names, i.e. $\text{Dom}_s(\theta) \stackrel{\Delta}{=} \{x | \theta(x) \in N_s\}$, and $\text{Im}_s(\theta)$ is written for the species names in the image of $\theta$, i.e. $\text{Im}_s(\theta) \stackrel{\Delta}{=} \text{Im}(\theta) \cap N_s$.

The translation to parts results in a set of genetic device templates $\Delta$ i.e. sets of lists over variables and names and sets of context sensitive substitutions $\Theta$. The target semantic object of a module is a partial function of the form $f(\tilde{A}) = (\Delta, \Theta)$ mapping actual parameters to the target semantic object of modules. Module definitions are then recorded in environments which are partial finite functions $\Gamma$ of the form $\Gamma(p) = f \cdot \Gamma\{p' \to f\}$ is the update of $\Gamma$ with a new binding to $p'$. The substitution of formal parameters $\tilde{u}$ for actual parameters $\tilde{A}$ in program P is written $P[\tilde{A}/\tilde{u}]$ and is defined inductively, with formal parameters and new variables as binders, using methods known in the art, except that nested multisets are flattened to a single multi-set following the substitution.

A function of the form $[[K]]_\theta = b$ is used for evaluating numerical constraints K, relative to a given substitution $\theta$, to a Boolean value b∈true/false. The full denotational semantics is given by a partial function of the form $[[P]]_\Gamma = (\Delta, \Theta)$, which maps a program P to a set $\Delta$ of genetic device templates and a set of $\Theta$ substitutions. It is defined inductively on programs as follows:

1. $[\![u{:}t(Q^t)]\!]_\Gamma \stackrel{\Delta}{=} (\{(u)\}, \Theta)$ where $$\Theta \stackrel{\Delta}{=} \left\{ \begin{array}{l} (\theta_i, \rho_i, \sigma_i, FS(Q_i), \sigma_i) \,| \\ u\theta_i{:}\, t(Q_i) \in K_b, Q^t\theta_i \subseteq Q_i, \\ \text{Dom}(\theta_i) = FV(u{:}\, t(Q^t)), \\ \rho_i = \text{Dom}_s(\theta_i), \sigma_i = FS(Q^t\theta_i) \end{array} \right\}$$

2. $[\![0]\!]_\Gamma \stackrel{\Delta}{=} (\emptyset, \{(\emptyset, \emptyset, \emptyset, \emptyset)\})$.

3. $[\![p(\tilde{u})\{P_1\}; P_2]\!]_\Gamma \stackrel{\Delta}{=} [\![P_2]\!]_{\Gamma[p \mapsto f]}$ where $f(\tilde{A}) \stackrel{\Delta}{=} \left[\!\!\left[ P_1\left\{\dfrac{\tilde{A}}{\tilde{u}}\right\}\right]\!\!\right]_\Gamma$.

4. $[\![p(\tilde{A})]\!]_\Gamma \stackrel{\Delta}{=} f(\tilde{A})$ where $f \stackrel{\Delta}{=} \Gamma(p)$.

5. $[\![P | C]\!]_\Gamma \stackrel{\Delta}{=}$ $(\Delta, \Theta_1 \cdot \Theta_2)$ where $(\Delta, \Theta_1) \stackrel{\Delta}{=} [\![P_\Gamma]\!]$ and $\Theta_2 = [\![C]\!]$ 6. $[\![P_1 P_2]\!]_\Gamma \stackrel{\Delta}{=} (\Delta_1 \cup \Delta_2, \Theta_1 \cdot \Theta_2)$ where $(\Delta_1, \Theta_1) \stackrel{\Delta}{=} [\![P_1]\!]_\Gamma$ and $(\Delta_2, \Theta_2) = [\![P_2]\!]_\Gamma$.

7. $[\![P_1; P_2]\!]_\Gamma \stackrel{\Delta}{=} (\{\delta_{1_i} \delta_{2_j}\}_{I \times J}, \Theta_1 \cdot \Theta_2)$ where $(\{\delta_{1_i}\}_I, \Theta_1) \stackrel{\Delta}{=} [\![P_{1_\Gamma}]\!]$ and $(\{\delta_{2_j}\}_I, \Theta_2) = [\![P_2]\!]_\Gamma$.

8. $[\![c[P]]\!]_\Gamma \stackrel{\Delta}{=} \left( \Delta, \left\{ \begin{array}{l} (\theta, \emptyset, \emptyset, \emptyset) \,| \\ (\theta, \rho, \sigma, \tau) \in \Theta \end{array} \right\} \right)$ where $(\Delta, \Theta) \stackrel{\Delta}{=} [\![P]\!]_\Gamma$.

9. $[\![\text{new } x \cdot P]\!]_\Gamma \stackrel{\Delta}{=} [\![P]\!][x'/x]_\Gamma$ for some fresh $x'$.

10. $[\![R]\!] \stackrel{\Delta}{=} \left\{ \begin{array}{l} (\theta_i, \text{Dom}_s(\theta_i), FS(R\theta_i), \emptyset) \,| \\ R\theta_i \in K_r, \text{Dom}(\theta_i) = FV(R) \end{array} \right\}$ 11. $[\![T]\!] \stackrel{\Delta}{=} \left\{ \begin{array}{l} (\theta_i, \text{Dom}_s(\theta_i), FS(T\theta_i), \emptyset) \,| \\ T^\downarrow \theta_i \in K_r, \text{Dom}(\theta_i) = FV(T) \end{array} \right\}$ 12. $[\![K]\!] \stackrel{\Delta}{=} \left\{ \begin{array}{l} (\theta_i, \text{Dom}_s(\theta_i), FS(T\theta_i), \emptyset) \,| \\ [\![K]\!]_{\theta_i} = \text{true}, \text{Dom}(\theta_i) = FV(K) \end{array} \right\}$.

13. $[\![C_1 | C_2]\!] \stackrel{\Delta}{=} (\Theta_1 \cdot \Theta_2)$ where $\Theta_1 \stackrel{\Delta}{=} [\![C]\!]_1$ and $\Theta_2 = [\![C]\!]_2$.

In the first case, the function results in a single sequence consisting of one part. The associated substitutions represent the possible solutions to the constraint that the part with the given properties must be in the database. The substitutions are required to be defined exactly on the variables mentioned in the program and to be infective over these. The excluded names are those which are associated with the part in the database but not stated explicitly in the program. The case 2, for the nil program gives the empty device template and a single context-sensitive substitution which is also empty.

The case 3, for module definition translates the program following the definition in the module environment updated with a new binding; this binding maps the module name to a function which, given a list of actual parameters, returns the device template and context-sensitive substitutions associated with the module body. The case 4, for module invocation looks up the given module identifier in the module environment and invokes the resulting function on the given actual parameters.

The case 5, for a program with constraints produces the part sequences associated with the semantics for the program, since the constraints do not give rise to any parts; the resulting substitutions arise from the composition of the substitutions for the program and for the constraints. The case 6, for parallel composition produces all the part sequences resulting from the first component together with all the part sequences resulting from the second component, i.e. the union of two sets, and the usual composition of substitutions. The case 7, for sequential composition differs only in the Cartesian product of part sequences instead of the union, i.e. all the sequences resulting from concatenating any sequence from the first program with any sequence from the second program are obtained.

The case 8, for compartments produces the part sequences from the contained program together with the substitutions, except that it "forgets" about the infective domain, used names and restricted names. Hence subsequent compositions of the compartment program with other programs will not be restricted in the use of names, reflecting the intuition that cross-talk is not a concern across compartment boundaries, as illustrated in the predator-prey case study (see discussion of FIGS. 12 and 13 below).

The case 9, for new variables substitutes the given variable in the following program with a variable which is fresh, i.e. which does not occur anywhere else in the surrounding program. The case 10, for reaction constraints gives a set of context-sensitive substitutions which, when applied to the reaction, gives rise to a reaction that is present in the reaction database. The variables on which the substitution must be infective are all the variables in the reaction, and the used species names are all the species names in the reaction. There are no excluded names. The case 11, is similar except that any compartment names in transport reactions are ignored. The case 12, is similar except that the chosen substitutions are those that make the numerical constraint true. The case 13, for constraint composition combines the context-sensitive substitutions arising from the two constraints.

One of the structures resulting from the compilations is a set of substitutions that can be applied to the device template and to the reaction template to find a final set of devices and reactions. In the example software implementation described herein, the substitutions are found by generating and solving a Prolog goal according to the principles set forth in the formal definitions of the translation to parts. The prolog database contains predicates prom(ID,P), rbs(ID,P), pcr(ID,P) and ter(ID,P) for representing each property p of a part with name ID. If a part has no properties, as is the case for the single ter part it is represented by a single clause with a distinguished "don't care" property.

A plurality of other predicates can be defined, a non-limiting list of examples includes: exclusiveNames(T, ID, Names, ExNames); namesDisjoint(N1, EN1, N2, EN2); noDuplicates(L). exclusiveNames(T, ID, Names, ExNames) holds true if ExNames is a list of exclusive names for the part identified by the type T and name ID, where Names are used for the names mentioned explicitly in the properties of the part. namesDisjoint(N1, EN1, N2, EN2) is used to enforce cross-talk avoidance in parallel and sequential compositions. namesDisjoint(N1, EN1, N2, EN2) holds true if N1, representing the names occurring on the left hand side of a composition operator is disjoint from EN2, representing the exclusive names of the program occurring on the right hand side of a composition operator and vice versa for EN1 and N2. noDuplicates(L) is used to enforce infectivity over species names of the resulting substitutions. It holds true if there are no duplicates in the list L. The Prolog implementation constructs a goal using the above predicates. Parts with properties give rise to a goal which is a conjunction of the relevant property predicates together with the exclusiveNames predicate which is used to get hold of the used and exclusive names associated with the part. Operations which use the composition operator on context-sensitive substitutions (e.g. parallel and sequential composition) give rise to the conjunction of the goals arising from the operands. An additional conjunction with the predicates noDuplicates and namesDisjoint, using the relevant variables from the goals arising from the operands, ensures that the requirements for context-free substitutions are satisfied. Once the complete goal is generated, it is executed using the Prolog engine which results in the desired substitutions. These can then be applied to the device template, resulting in a plurality 406 of possible sets of parts for the genetic devices which can be input into a biological manufacturing process 408.

Figure 5:
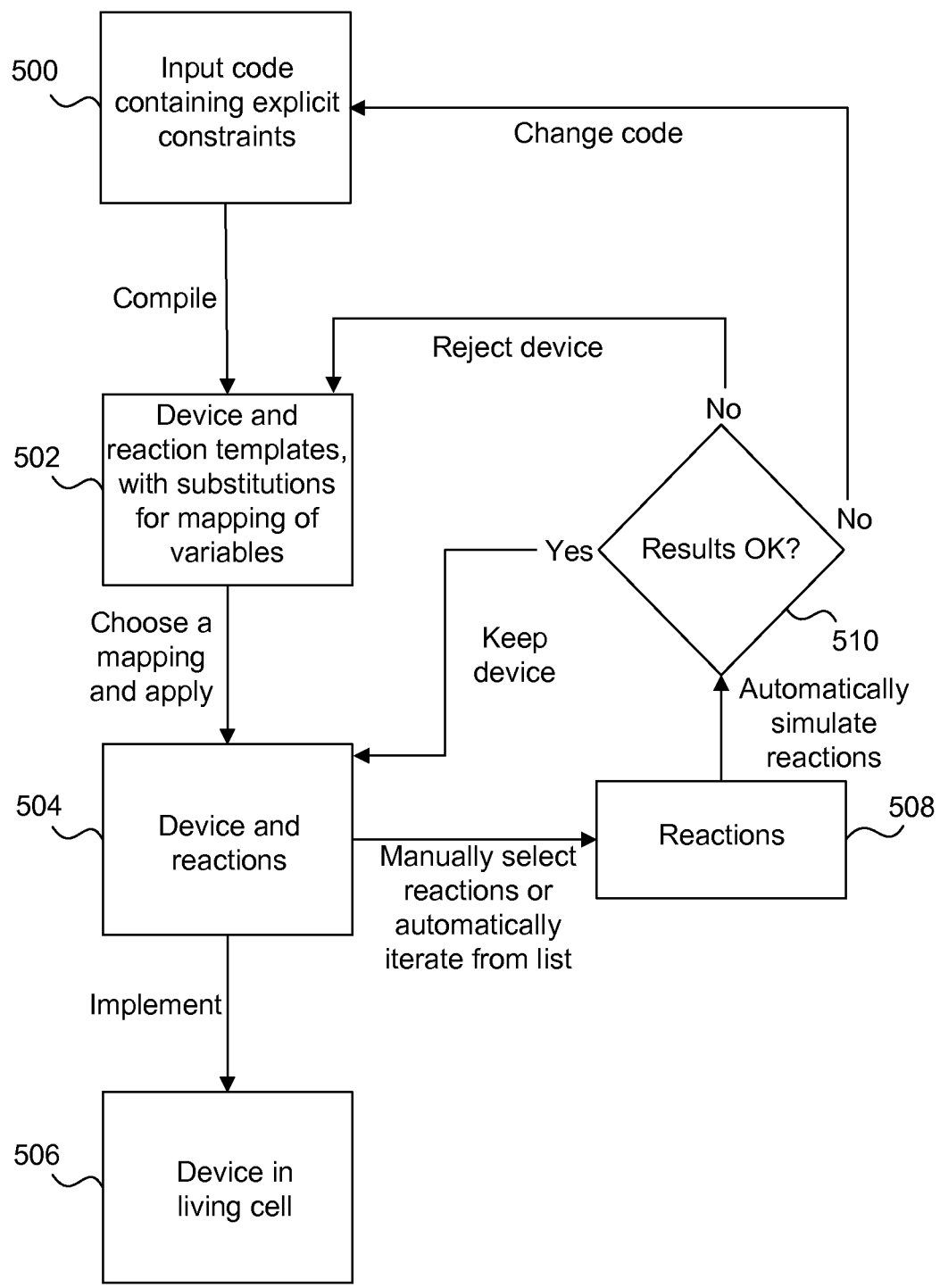
FIG. 5 is a flow diagram of a method of creating a genetic device.

FIG. 5 is a flow diagram of a method of creating a genetic device. A program comprising code 500, formed using a programming language such as that described above is input into a compiler. The compiler resolves the constraints in the code using the properties described in the parts database 300. Executing a Prolog goal (as described above) yields a plurality of substitutions together with a device template and a reaction template 502. Choosing a substitution and applying it to the device template and the reaction template yields a concrete device and a set of reactions 504. The concrete device can be implemented in a living cell 506. The reactions can optionally be selected 508 and the reactions can then be automatically simulated and the simulation results 510 taken into account.

Simulation may be used to investigate a variety of different issues before implementation in a living cell such as a bacterium for example. In an example the potential impact of genetic devices on the host physiology, such as the metabolic burden can be modeled. This can be implemented by including an explicit model of host physiology when generating the reactions of a given program for simulation.

In the absence of the reactions database the plurality of different genetic devices can be implemented using a genetic device manufacturing system on a trial and error basis.

If the results of the simulation 510 are satisfactory the device can then be implemented in a living cell. Alternatively if the results 510 of the simulation are unsatisfactory an alternative substitution can be selected from the plurality of substitutions 502. If none of the plurality of substitutions are satisfactory then the code 500 can be adjusted.

Figure 6:
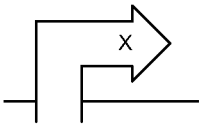
FIG. 6 shows graphical representations of some of the types of parts used in an example database of DNA sequences.
Figure 6:
Figure 6:
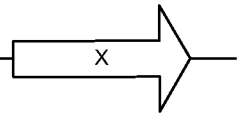
Figure 6:
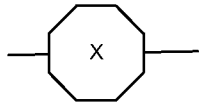

FIG. 6 shows graphical representations of some types of parts used in an example database of DNA sequences. The parts 600 are represented by graphical representations 602. An example of a part with the property of a promoter 604 is shown and its corresponding graphical representation. An example of a part with the property of a ribosome binding site 606 is shown and its corresponding graphical representation. An example of a part with a protein coding region 608 is shown and its corresponding graphical representation. An example of a part with the property of terminator 610 is shown and its corresponding graphical representation.

Figure 7:
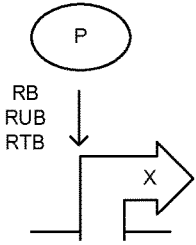
FIG. 7 is a table of example parts and their properties together with examples of associated reactions.
Figure 7:
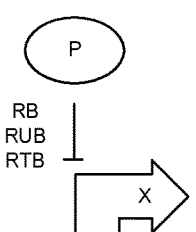
Figure 7:
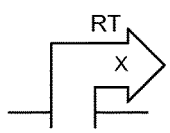
Figure 7:
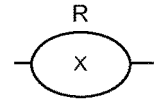
Figure 7:
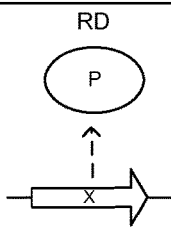

FIG. 7 is a table of example parts 700 and their properties together with examples of associated reactions. Graphical representations 702 for each part, property and reactions combination are given. The table comprises the positive 704 and negative 706 properties of promoters. The constitutive rate of transcription of promoters in absence of transcription factors 708. The rate of translation of mRNA at a ribosome binding site 710 and the protein being coded by a protein coding region, together with a rate of protein degradation 712.

The positive 704 and negative 706 properties of promoters each give rise to three reactions: binding of the transcription factor, unbinding of the transcription factor and the production of mRNA in the bound state. The constitutive rate of transcription of promoters in absence of transcription factors 708 yields a reaction producing mRNA in the unbound state and a reaction for the degradation mRNA at a rate rdm. The mRNA can be used by neighboring parts in the sequence. The rate property of a ribosome binding site 710 yields a reaction producing a protein from mRNA. However, neither the mRNA nor the protein is known until the ribosome binding site is placed next to a protein coding region. The result is therefore effectively a function of the protein coding region. The mRNA is obtained from the ribosome binding site, protein coding region and a subsequent terminator, while the protein P is obtained from the protein coding region.

The codes property of the protein coding region 712 gives rise to a protein degradation reaction. The evaluation of the codes property of the protein coding region also provides the species name P for the protein which can then be used by neighboring parts. The rate used for mRNA degradation can be defined globally but may be adjusted manually for individual cases. In an alternative embodiment quantities such as mRNA and protein degradation rates can be stored in the reaction database.

The translation to reactions is complicated further in the presence of compartments and transport since degradation reactions may need to be placed in multiple compartments that do not necessarily express the given protein. To address this the reaction translation function returns separately a reaction template, which is expressed as an LBS program, and a set of deduced degradation reactions. After translation, these degradation reactions can be placed in the relevant compartments and composed with the LBS program.

A reaction template L is defined as consisting of reactions and transport reactions in parallel, taking place inside some hierarchy of compartments. Formally:

$$L::=R:T:0:L_1|L_2:c[L]$$

Given a set L of reaction templates, (par L) denotes their parallel composition; the order is irrelevant as this operator is commutative. The translation function takes the following form:

$$[[P]]_\Gamma = (L, D, M, Pr, F, G, H)$$

where
- L is a reaction template.
- D is a set of degradation reactions.
- $M \subset U$ is a set of mRNA names.
- $Pr \subset U$ is a set of protein names.
- F is a function of the form f(m, p)=R mapping pairs (m, p)∈U×U of mRNA and protein names to a reaction.
- G is a function of the form g(m)=R mapping an mRNA species name m∈U to a reaction.
- H is a function of the form h(p)=R mapping a protein name p∈U to a reaction.

The translation is defined inductively as follows, where given a global mRNA degradation rate rdm 1. $[\![u: prom(Q)]\!]_\Gamma \triangleq \begin{pmatrix} par\{reacs(q) \mid q \in Q\} \mid m \rightarrow^{rdm}, \\ \{m\}, \emptyset, \emptyset, \emptyset, \emptyset, \emptyset \end{pmatrix}$ where $reacs(con(rt)) \triangleq g \rightarrow^{rt} g + m$.

$reacs\left(pos\begin{pmatrix} S, rb, \\ rub, rtb \end{pmatrix}\right) \triangleq$ $g + S \rightarrow^{rb} g - S | g - S \rightarrow^{rub} g + S | g - S \rightarrow^{rtb} g - S + m$ $reacs\left(neg\begin{pmatrix} S, rb, \\ rub, rtb \end{pmatrix}\right) \triangleq$ $g + S \rightarrow^{rb} g - S | g - S \rightarrow^{rub} g + S | g - S \rightarrow^{rtb} g - S + m$ with g and m fresh.

2. $[\![u: rbs(\{rate(r)\})]\!]_\Gamma \triangleq (0, \emptyset, \emptyset, \emptyset, \{f\}, \emptyset, \emptyset)$ where $f(m, p) \triangleq m \rightarrow^r p$.

3. $[\![u: pcr(\{codes(p, r)\})]\!]_\Gamma \triangleq (0, \{p \rightarrow^r\}, \emptyset, \{p\}, \emptyset, \emptyset, \emptyset)$.

4. $[\![u:ter]\!]_\Gamma \triangleq (0, \emptyset, \emptyset, \emptyset, \emptyset, \emptyset, \emptyset)$.

5. $[\![0]\!]_\Gamma \triangleq (0, \emptyset, \emptyset, \emptyset, \emptyset, \emptyset, \emptyset)$.

6. $[\![p(\tilde{u})\{P_1\}; P_2]\!]_\Gamma \triangleq$ $[\![P_2]\!]_{\Gamma[p \mapsto f]}$ where $f(\tilde{A}) \triangleq [\![P_1\{\tilde{A}/\tilde{u}\}]\!]$.

7. $[\![p(\tilde{A})]\!]_\Gamma \triangleq f(\tilde{A})$ where $f \triangleq \Gamma(p)$.

8. $[\![P \mid C]\!]_\Gamma \triangleq \begin{pmatrix} L_1 \mid L_2, D, M, \\ Pr, F, G, H \end{pmatrix}$ where $\begin{pmatrix} L_1, D, M, \\ Pr, F, G, H \end{pmatrix} \triangleq [\![P]\!]_\Gamma$ and $L_2 \triangleq [\![C]\!]$.

9. $[\![P_1 P_2]\!]_\Gamma \triangleq \begin{pmatrix} L_1 \mid L_2, D_1 \cup D_2, M_1 \cup M_2, Pr_1 \cup Pr_2, \\ F_1 \cup F_2, G_1 \cup G_2, H_1 \cup H_2 \end{pmatrix}$ where $\begin{pmatrix} L_1, D_1, M_1, Pr_1, \\ F_1, G_1, H_1 \end{pmatrix} \triangleq [\![P_1]\!]_\Gamma$ and $\begin{pmatrix} L_2, D_2, M_2, \\ Pr_2, F_2, G_2, H_2 \end{pmatrix} \triangleq [\![P_2]\!]_\Gamma$.

10. $[\![P_1 \| P_2]\!]_\Gamma \triangleq \begin{pmatrix} L_1|L_2|L, D_1 \cup D_2, \\ M, Pr, F'_1 \cup F'_2, G, H \end{pmatrix}$ where $(L_1, D_1, M_1, Pr_1, F_1, G_1, H_1) \triangleq [\![P_1]\!]_\Gamma$, $(L_2, D_2, M_2, Pr_2, F_2, G_2, H_2) \triangleq [\![P_2]\!]_\Gamma$, $L \triangleq par\left\{\begin{matrix} g(m) \mid g \in G_2, \\ m \in M_1 \end{matrix}\right\} \cup par\left\{\begin{matrix} h(p) \mid h \in H_1, \\ p \in Pr_2 \end{matrix}\right\}$, $M \triangleq \begin{cases} M_1 & \text{if } M_2 = \emptyset \\ M_2 & \text{otherwise} \end{cases}$ $Pr \triangleq \begin{cases} Pr_2 & \text{if } Pr_1 = \emptyset \\ Pr_1 & \text{otherwise} \end{cases}$ $(F'_1, H'_1) \triangleq \begin{cases} (F_1, H_1) & \text{if } Pr_2 = \emptyset \\ (\emptyset, \emptyset) & \text{otherwise} \end{cases}$ $(F'_2, G'_2) \triangleq \begin{cases} (F_2, G_2) & \text{if } M_1 = \emptyset \\ (\emptyset, \emptyset) & \text{otherwise} \end{cases}$ -continued $$G \triangleq \left\{ g \mid g(m) \triangleq f(m, p), \atop f \in F_1, p \in Pr_2 \right\} \cup G_1 \cup G_2'$$

$$H \triangleq \left\{ h \mid h(p) \triangleq f(m, p), \atop f \in F_2, m \in M_1 \right\} \cup H_2 \cup H_1'.$$

11. $[\![c[P]]\!]_\Gamma \triangleq \begin{pmatrix} c[L], D, M, \\ Pr, F, G, H \end{pmatrix}$ where $\begin{pmatrix} L, D, M, Pr, \\ F, G, H \end{pmatrix} \triangleq [\![P_1]\!]_\Gamma$.

12. $[\![\text{new } x \cdot P]\!]_\Gamma \triangleq [\![P[x'/x]]\!]_\Gamma$ for some fresh $x'$.

13. $[\![R]\!] \triangleq R$.

14. $[\![T]\!] \triangleq T$.

15. $[\![K]\!] \triangleq 0$.

16. $[\![C_1 \mid C_2]\!] \triangleq [\![C_1]\!] \mid [\![C_2]\!]$.

The resulting reaction template may generally contain variables, and each substitution arising from the translation to parts can be applied to the reaction template in order to obtain a set of reactions, expressed as an LBS program, for each device. Note that the same fresh variables must be chosen for both the translation to device templates and the corresponding translation to reaction templates.

FIGS. 8A to 8D are schematic diagrams of sequences of parts showing how logical variables may be used. On the most basic level shown in FIG. 8A a program can be a sequence of part identifiers together with their types. The part identifiers are represented graphically as 800, 801, 802, 803 with the part IDs written inside the graphical representations. The symbol : is used to denote the type of a part and the symbol ; is used to denote a sequential composition operator used to put the parts together in a sequence. In the example shown in FIG. 8A a transcription unit that expresses the protein tetR in a negative feedback loop is given. Parts and their types can be explicitly specified:

r0040:prom; b0034:rbs; c0040:pcr; b0015:ter however explicit specification of parts requires that the programmer is aware of the properties of the specified parts.

Figure 8A:
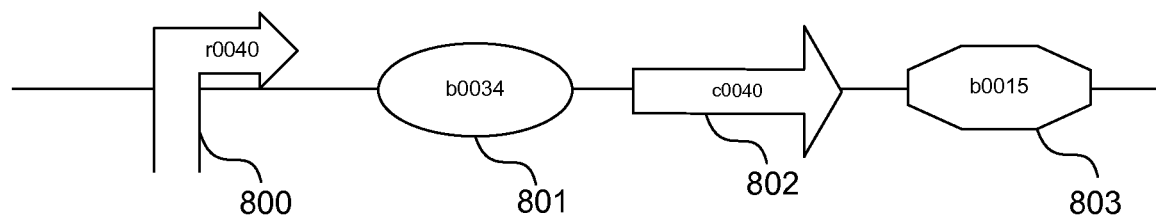
FIGS. 8A to 8D are schematic diagrams of a sequence of parts showing how logical variables may be used.
Figure 8B:
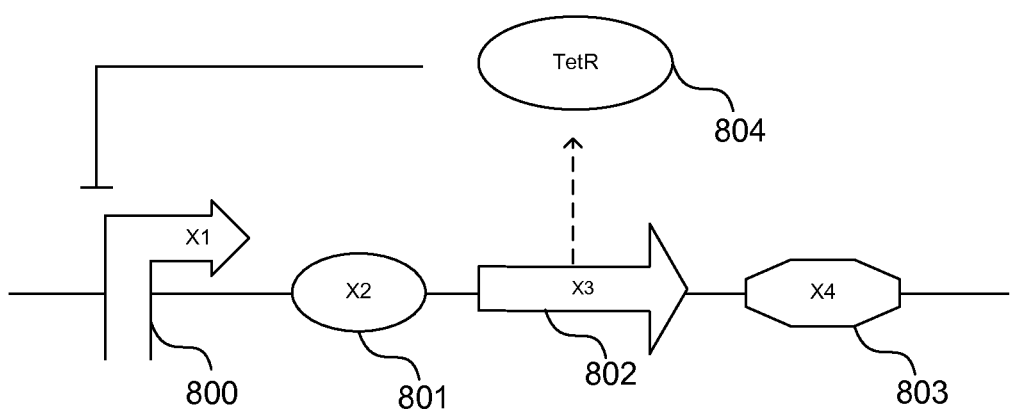

The level of abstraction of the program can be increased as is shown in FIG. 8B by using variables and properties rather than specifying a sequence of specific parts. The graphical representations 800, 801, 802, 803 now contain variable names rather than explicit part IDs. The example described above can be written as:

X1:prom<neg(tetR)>; X2:rbs; x3:pcr<codes(tetR)>; X4:ter where the angle brackets delimit one or more properties and the upper-case identifiers such as X1 represent variables. Variables represent undetermined part names or species. The compiler may produce several results. In this example, the part 802 must yield part 804 TetR.

Figure 8C:
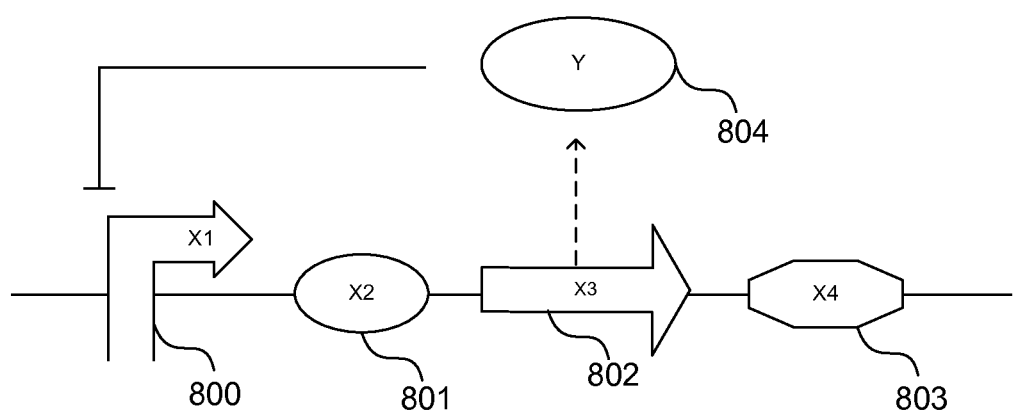
Figure 8D:
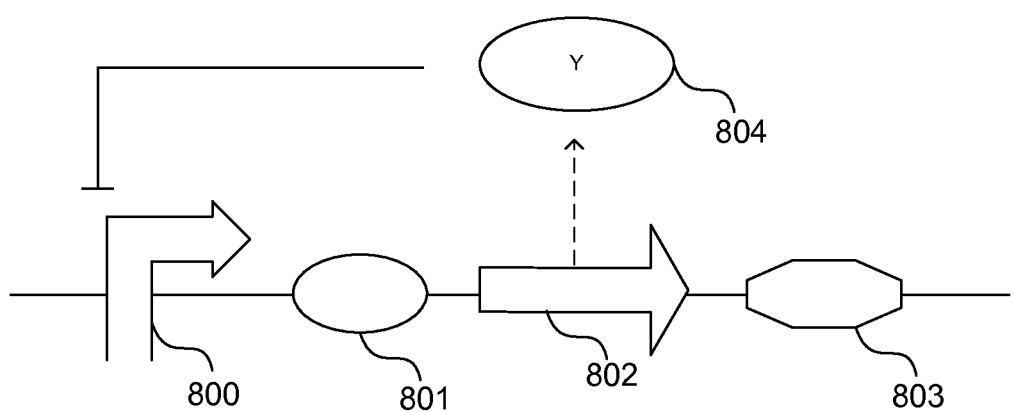

The fixed species name 804, in the above example tetR, can be replaced with a new variable Y which results in a program which expresses any transcription unit behaving as a negative feedback device as is shown in FIG. 8C. In addition as shown in FIG. 8D when variables are only used once their names are of no significance and can be replaced with a wild card. When there is no risk of ambiguity the wild card can be omitted and the program 108 can be written in the concise form:

prom<neg(Y)>; rbs; pcr<codes(Y)>; ter

Distinct variables must take distinct values in order to prevent devices with undesired behaviors being returned. However in cases when distinct variables can take the same value it is possible to alter the semantics of the language and the compiler on a case by case basis.

Figure 9:
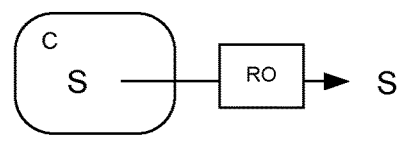
FIG. 9 is a table of example reactions and corresponding graphical representations.
Figure 9:
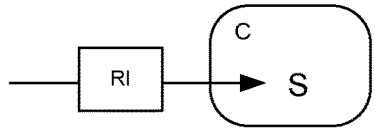
Figure 9:
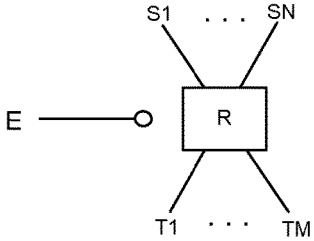

FIG. 9 is a table of example reactions 900 and their corresponding graphical representations 901. Transport reactions 902 and 904 are represented as well as enzymatic reactions 906. The transport of some species S out of a compartment c is specified at a rate RO and is described graphically 902. The transport of some species S into a compartment C at some rate R1 is also described graphically 904. The reaction of some enzyme E with reactants S1 ... SN at a rate R to synthesize products T1 ... TM is also described graphically 906.

Some possible embodiments of a system to create genetic devices will now be described with references to FIGS. 10-13. A repressilator is a synthetic genetic regulatory network reported in Elowitz and Leibler 2000 "A synthetic oscillatory network of transcriptional regulators, Nature, 403, 335-338". A genetic circuit was designed to exhibit a stable oscillation which is reported via the expression of green fluorescent protein. A repressilator consists of three genes connected in a feedback loop such that they negatively regulate each other. The first gene in the circuit expresses a protein A, which represses the second gene; the second gene expresses some protein B, which represses the third gene; and the third gene expresses some protein C, which represses the first gene.

Figure 10:
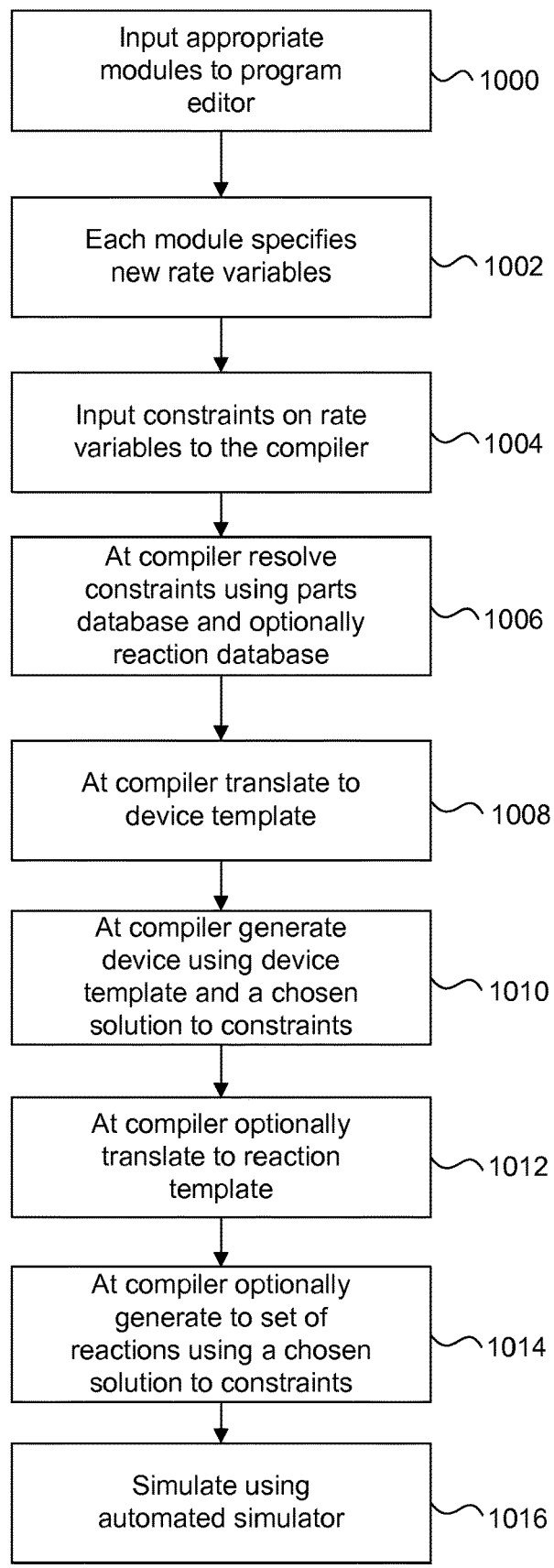
FIG. 10 is a flow diagram of a program for specifying a genetic repressilator circuit.

FIG. 10 is a flow diagram of a program for specifying a genetic repressilator circuit. A negative gate module is used to describe the behavior of each gene and the modules are input to a computer system using a program editor 1000. For each module a new set of rate variables is used 1002. Optionally constraints on the rate variables can be specified 1004. The input and outputs of each module are required 1006. The program is compiled by resolving constraints 1006 using the parts database and optionally the reaction database; a device template is generated 1008 and a chosen solution to the constraints is used to generate a device from the device template 1010. Optionally the program can also be compiled to a reaction template 1012 and subsequently to a set of reactions using a chosen solution to the constraints 1014. The set of reactions can be simulated using the automated simulator 1016.

The negative gate module, input to the computer system using a program editor 1000, comprises a promoter which has a constitutive rate of transcription in the absence of transcription factors con(RT), and which is negatively regulated by an input protein or protein complex i, with binding and unbinding rates RB and RUB respectively and rate of transcription of the bound state RTB. The negative gate module also comprises a ribosome binding site RBS with a binding rate R and a protein coding region pcr which codes for an output protein o at a rate RD.

The new operator is used to ensure that for each module a new set of rate variables is used 1002. This is used in the repressilator example as the same module is implemented three times but it is not required that the rates are the same for all three instances.

Appropriate ranges for quantitative parameters can be found through simulations. Optionally the ranges for quantitative parameters can be input to the gate module as constraints 1004 on the rate variables. The inputs and outputs are then specified 1006. In the repressilator example the first gate module has the input C and the output A, the second gate module has the input A and the output B and the third gate module has the input B and the output C. The input modules are invoked using a sequential composition operator.

In the repressilator example without additional constraints 1004 and with a database of possible parts as shown in FIG. 3, 24 possible devices are generated. As distinct variables take distinct values this excludes devices which act as self inhibiting gates. In order to select the device with the most appropriate behavior it is optionally possible to simulate the associated reactions.

In the case of the repressilator a number of the returned devices do not display the expected oscillations. This can be caused for example by a low rate of transcription factor unbinding such that once a transcription factor is bound the promoter is likely to remain repressed. Appropriate ranges for quantitative parameters in which the expected oscillations do occur can be found using simulations 1016. The results of these simulations can then be used to automatically refine the constraints on the rate variables which cause the compiler to return significantly fewer devices.

Figure 11:
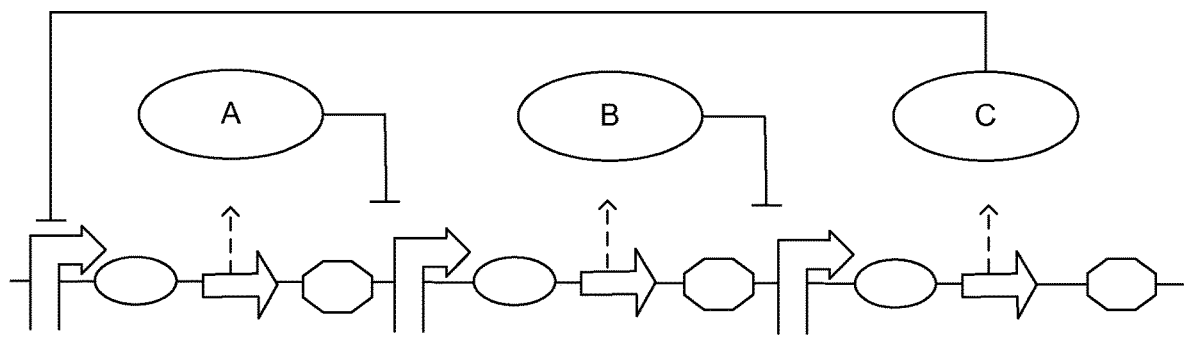
FIG. 11 is an example of a program for specifying a genetic repressilator circuit.

A graphical representation of a general repressilator system is shown in FIG. 11. The first gene comprises a promoter negatively regulated by protein C, a ribosome binding site and a protein coding region which codes for protein A. The terminator shows the end of the sequence. A second gene comprises a promoter which is negatively regulated by protein A and comprises a ribosome binding site, a protein coding region which codes for protein B and terminator. A third gene comprises a promoter which is negatively regulated by protein B a ribosome binding site, a protein coding region which codes for protein C and a terminator. This completes a feedback loop.

Figure 12:
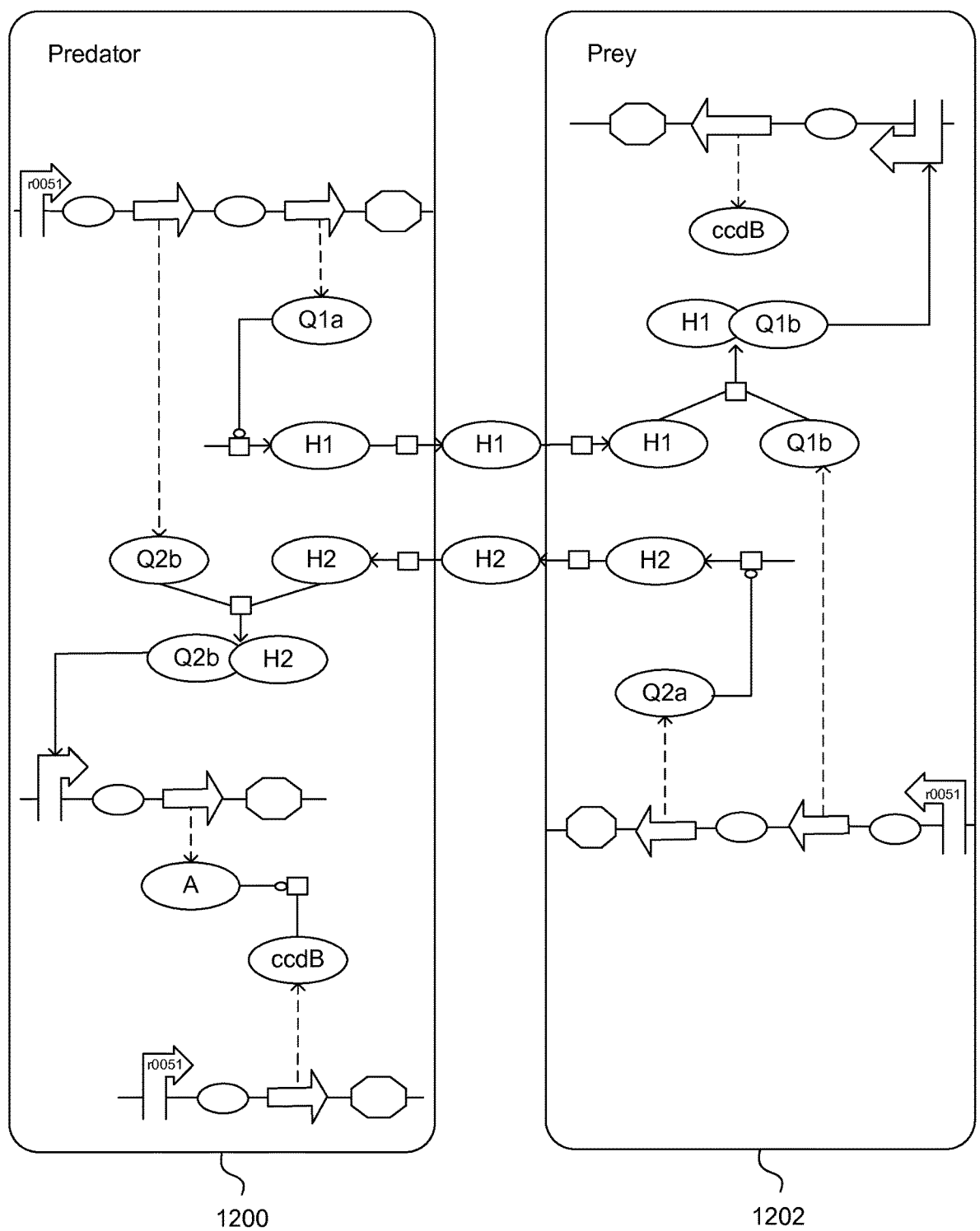
FIG. 12 is a graphical representation of a program for a predator-prey genetic circuit.

A second embodiment comprises the computer system 100 having a program 108 which represents an *Escheria-Coli* predator-prey system (as reported in Balagaddé, F., Song, H., Ozaki, J., Collins, C., Barnet, M., Arnold, F., Quake, S. & You, L. 2008 "A synthetic *Escherichia coli* predator-prey ecosystem", Molecular Systems Biology, 4, 187). This may be used to identify appropriate genetic parts for forming such a biological system. FIG. 12 is a graphical representation of a program for a predator-prey genetic system. It is based on two quorum-sensing systems, one enabling predator cells to induce an expression of death gene in prey cells and the other enabling prey cells to inhibit the expression of a death gene in the predator. In the predator 1200, Q1*a* is constitutively expressed and synthesizes H1, which diffuses to the prey 1202 where it dimerizes with the constitutively expressed Q1*b*. This dimer in turn induces expression of the death protein ccdB. Symmetrically the prey constitutively expresses Q2*a* for synthesizing H2, which diffuses to the predator where it dimerizes with the constitutively expressed Q2*b*. Instead of inducing cell death this dimer induces expression of an antidote A which interferes with the constitutively expressed death protein.

Figure 13:
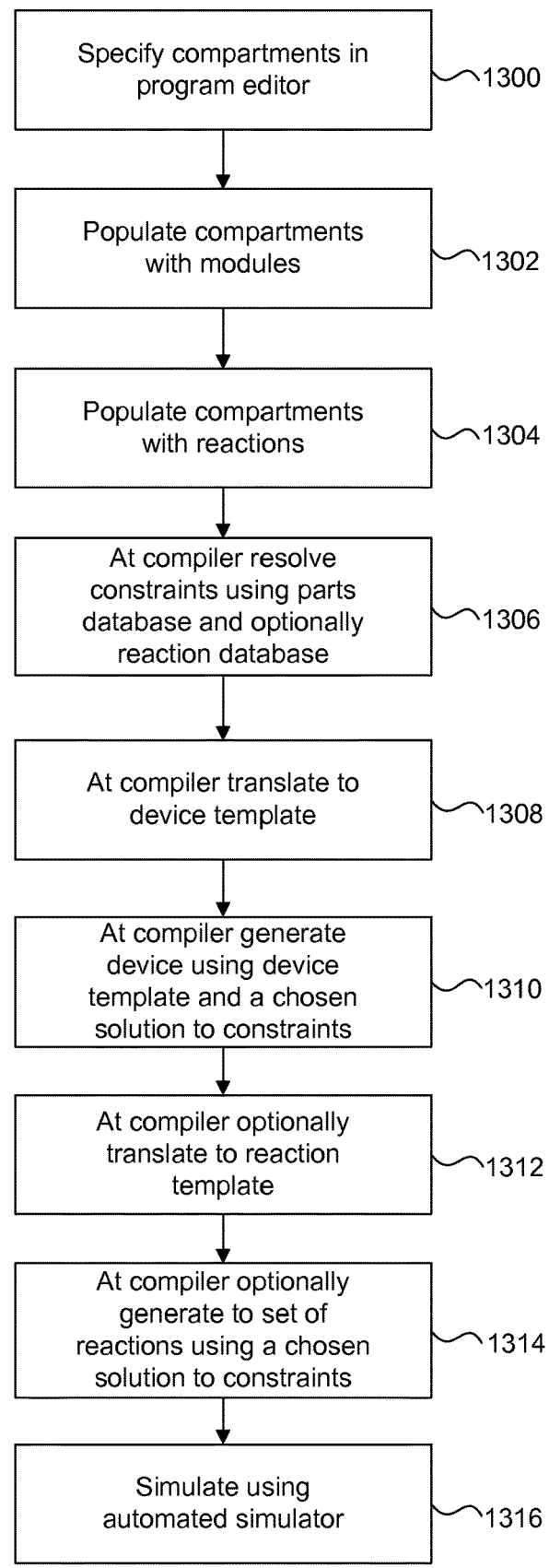
FIG. 13 is a flow diagram of a program for a predator-prey genetic circuit.

FIG. 13 is a flow diagram of a program for a predator-prey genetic circuit. Compartments are specified 1300, which are populated with modules 1302 and reactions 1304. The compartments are composed using a parallel composition operator. The program is then compiled by resolving constraints 1306 using the parts database and optionally the reaction database; a device template is generated 1308 and a chosen solution to the constraints is used to generate a device from the device template 1310. Optionally the program can also be compiled to a reaction template 1312 and subsequently to a set of reactions using a chosen solution to the constraints 1314. The set of reactions can be simulated using the automated simulator 1316.

A transport module defines transport reactions across two compartments 1300, representing predator and prey boundaries. Compartments can be used in systems where a part may be used for more than one function in different parts of the system. For example, in the predator prey system a promoter is used both for regulating ccdA in the predator and for regulating ccdB in the prey. Without the compartment boundaries undesired cross-talk may occur between parts in different areas of the system. If compartments are not used then the compiler detects the cross-talk and will report that no devices can be found.

The predator and prey are programmed in separate modules 1302, which are used to populate the compartments. A third module links the predator and prey by defining transport reactions. Reactions 1304 are composed with each other and with the gate modules through the constraint composition module which is also used for quantitative constraints. Reactions 1304 do not add any parts to the system but they restrict the possible choices of proteins and hence of parts, in a similar fashion to the specified constraints in the repressilator embodiment described above.

In some embodiments, the semantics of the programming language used are arranged to ensure that a part may only be used if its 'implicit' properties do not contain species which are present in the same compartment as the part. Implicit properties are properties of a part which are not explicitly specified in the program but which are present in the parts database. In an example, a part may be positively regulated by a protein hence that part may not be used in a compartment where the protein is present if the regulation has not been specified explicitly through part properties.

The main body of the program invokes the three modules while putting predator and prey inside their respective compartments using a compartment operator. The modules are composed using a parallel composition operator, which results in union of the part sequences of operands. This is the case when devices are implemented on different plasmids or even in different cells as in the case in the predator prey system.

Compilation of the predator prey system results in a number of possible devices and associated reactions which can be simulated 1316 to find a genetic device with appropriate behavior which can be implemented in cells.

Figure 14:
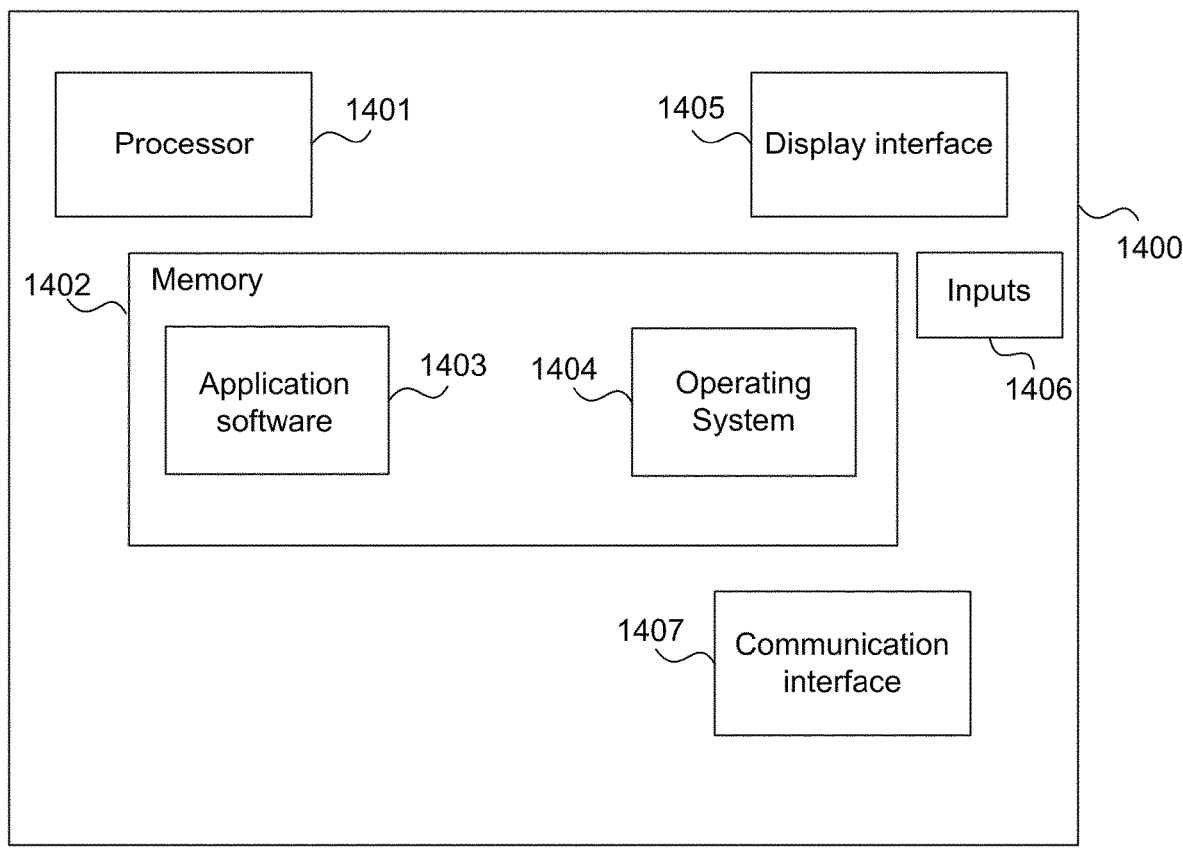
FIG. 14 illustrates an exemplary computing-based device in which embodiments of a system for creating genetic devices may be implemented.

FIG. 14 illustrates various components of an exemplary computing-based device 1400 which may be implemented as any form of a computing and/or electronic device, and in which embodiments of a system for creating genetic devices may be implemented.

The computing-based device 1400 comprises one or more inputs 1406 which are of any suitable type for receiving media content, Internet Protocol (IP) input or any form of input. The device also comprises communication interface 1407.

Computing-based device 1400 also comprises one or more processors 1401 which may be microprocessors, controllers or any other suitable type of processors for processing computing executable instructions to control the operation of the device in order to generate genetic devices. Platform software comprising an operating system 1404 or any other suitable platform software may be provided at the computing-based device to enable application software 1403 to be executed on the device.

The computer executable instructions may be provided using any computer-readable media, such as memory 1402. The memory is of any suitable type such as random access memory (RAM), a disk storage device of any type such as a magnetic or optical storage device, a hard disk drive, or a CD, DVD or other disc drive. Flash memory, EPROM or EEPROM may also be used.

An output 1407 is also provided such as an audio and/or video output to a display system integral with or in communication with the computing-based device. The display system may provide a graphical user interface, or other user interface of any suitable type although this is not essential.

The term 'computer' is used herein to refer to any device with processing capability such that it can execute instructions. Those skilled in the art will realize that such processing capabilities are incorporated into many different devices and therefore the term 'computer' includes PCs, servers, mobile telephones, personal digital assistants and many other devices.

The methods described herein may be performed by software in machine readable form on a tangible storage medium. The software can be suitable for execution on a parallel processor or a serial processor such that the method steps may be carried out in any suitable order, or simultaneously.

This acknowledges that software can be a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought.

The term 'comprising' is used herein to mean including the method blocks or elements identified, but that such blocks or elements do not comprise an exclusive list and a method or apparatus may contain additional blocks or elements.

It will be understood that the above description of a preferred embodiment is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention.

The invention claimed is:

1. A method of creating a genetic device including a deoxyribonucleic acid (DNA) sequence that encodes genetic parts that function together when introduced into a host cell to satisfy a specified set of constraints, the method comprising:
    establishing a connection to a database of genetic parts, an entry in the database comprising a part type and at least one part property;
    receiving, by a program editor, input specifying a plurality of part designs at least some of which comprise the at least one part property expressed in terms of a logical variable and constraints on the logical variable without exact specification of a DNA sequence to be used;
    resolving, at a compiler, the constraints using a constraint resolution engine to provide at least one sequence of the genetic parts from the database of genetic parts, wherein the sequence of the genetic parts satisfies the constraints, the constraints being one or more biological behaviors, chemical reactions, or a combination thereof, wherein the resolving includes:
    identifying a genetic part,
    identifying an empty device template and an empty part substitution,
    binding a module name to a function given one or more parameters,
    looking up the module name,
    invoking the function bound to the module name,
    producing a part sequence, producing a union of two part sequences,
    producing a sequential composition of the two part sequences,
    creating a compartment-specific part sequence,
    substituting a new variable for the logical variable, the new variable not occurring elsewhere in the sequence of genetic parts,
    creating a set of context-sensitive substitutions,
    ignoring compartment names in transport reactions,
    identifying substitutions that satisfy a numerical constraint, and
    combining context-sensitive substitutions arising from the numerical constraint;
    presenting the at least one sequence of the genetic parts which satisfy the constraint; and
    manufacturing the at least one sequence of genetic parts which satisfy the constraint.

2. A method as claimed in claim 1, wherein the constraints on the logical variable comprise implicit constraints associated with a part design, wherein the implicit constraints are those constraints on a part that arise from having multiple occurrences of a same logical variable in the input.

3. A method as claimed in claim 1 which further comprises, at the compiler, compiling the part designs and the constraints to reactions.

4. A method as claimed in claim 3 which further comprises, performing a simulation of the reactions provided by the compiler and selecting one of the sequences of parts on a basis of the simulation.

5. A method as claimed in claim 3, wherein the compiler uses semantics to associate at least some reactions of a part with properties of neighboring parts in the sequence of the genetic parts.

6. A method as claimed in claim 1 which further comprises, establishing a connection to a database of reactions for resolving the constraints; and
    wherein the program editor is arranged to receive the input such that the input specifies at least some of the constraints on the logical variable using one or more reactions from the database of reactions.

7. A method as claimed in claim 1, wherein the program editor is arranged to receive the input such that the input specifies at least some of the constraints on the logical variable using biological compartments where a biological compartment specifies a location of a plurality of parts within the biological compartment and prevents cross talk between parts inside the biological compartment and parts outside the biological compartment.

8. A method as claimed in claim 7 which further comprises, at the compiler, using specified constraints to ensure piece-wise injectivity of substitutions for the logical variable so that distinct logical variables within a same biological compartment are substituted with distinct parts.

9. A method as claimed in claim 7, which further comprises, at the compiler, using specified constraints to ensure that a part is used if implicit properties of the part are devoid of species which are present in a same biological compartment as the part, wherein the implicit properties are those properties of the part without explicit specification in the input, but which are present in the database entry for the part.

10. A method of creating a genetic device, the method comprising:
    establishing a connection to a database of genetic parts, an entry of the database including an identifier of a deoxyribonucleic acid (DNA) sequence and at least one part property that includes a binding rate specified for gene expression of the DNA sequence;
    receiving, by a program editor, input specifying a plurality of genetic parts, the plurality of genetic parts including at least one unspecified genetic part that is represented by use of a logical variable together with one or more properties without exact specification of a DNA sequence to be used, wherein the one or more properties are expressed in terms of logical variables that impose constraints on the unspecified genetic part, the constraints including a rate having a specified range;
    resolving, at a compiler, the constraints using specified semantics to provide at least one possible genetic device template comprising a list of part variables and substitutions on the part variables that, when applied to the genetic device template, results in a list of genetic parts which satisfies the constraints, wherein the specified semantics comprise:
        identifying a genetic part,
        identifying an empty device template and an empty part substitution,
        binding a module name to a function given one or more parameters,
        looking up the module name,
        invoking the function bound to the module name,
        producing a part sequence,
        producing a union of two part sequences,
        producing a sequential composition of the two part sequences,
        creating a compartment-specific part sequence,
        substituting a new variable for the logical variable, the new variable not occurring elsewhere in the sequence of genetic parts,
        creating a set of context-sensitive substitutions,
        ignoring compartment names in transport reactions,
        identifying substitutions that satisfy a numerical constraint, and
        combining context-sensitive substitutions arising from the numerical constraint;
    establishing a connection to a database of reactions each associated with one or more constraints;
    translating, at the compiler, the at least one possible genetic device template and the constraints provided by the input to at least one reaction from the database of reactions;
    receiving a selection of the at least one reaction for a simulation;
    conducting the simulation after the constraints have been satisfied, the simulation being based at least in part on an explicit host physiology;
    evaluating the at least one possible genetic device template based at least in part on results of the simulation; and
    manufacturing a genetic device selected based at least in part upon the results of the simulation.

11. A method as claimed in claim 10, wherein the compiler uses semantics to enable at least some reactions of a genetic part to depend on properties of neighboring parts in sequences of genetic parts.

12. A method as claimed in claim 10 further comprising, when the results of the simulation indicate that there are no valid substitutions of genetic parts for the logical variable in the possible genetic device template, modifying the input.

13. A system comprising:
    an input arranged to connect to a genetic parts database of parts representing deoxyribonucleic acid (DNA) sequences, each part comprising a part type selected from a group comprising a promoter, a ribosome binding site, and a protein coding region;
    a unique identifier of a DNA sequence;
    at least one part property selected from a group comprising activation by a transcription factor, inhibition by a transcription factor, binding rate, unbinding rate, interaction with a protein, and rate of protein degradation;
    a program editor configured to receive a program input specifying a plurality of the parts, an ordering of the parts, and at least one constraint on at least one of the parts;
    a memory storing rules embodying denotational semantics of a language of the program input;
    a compiler arranged to resolve the at least one constraint, the at least one constraint consisting of biological behaviors, reactions of DNA sequences, or a combination thereof, using the at least one part property while accounting for interactions between DNA sequences of the parts received in the program input to provide a device template comprising at least one sequence of parts from the genetic parts database which satisfies the at least one constraint, the at least one constraint being specified without identification of sequences of the DNA sequences of the parts, wherein the resolving includes:
        identifying a genetic part,
        identifying an empty device template and an empty part substitution,
        binding a module name to a function given one or more parameters, looking up the module name, invoking the function bound to the module name, producing a part sequence, producing a union of two part sequences, producing a sequential composition of the two part sequences, creating a compartment-specific part sequence, substituting a new variable for the logical variable, the new variable not occurring elsewhere in the sequence of genetic parts, creating a set of context-sensitive substitutions, ignoring compartment names in transport reactions, identifying substitutions that satisfy a numerical constraint, or combining context-sensitive substitutions arising from the numerical constraint;

an automated simulator configured to simulate a plurality of sequences of parts generated by the compiler; and a genetic device manufacturing system configured to create a sequence of parts of the plurality of sequences of parts in a living cell, the sequence of parts selected based at least in part on results of the automated simulator.

14. A system as claimed in claim 13, wherein the compiler is arranged to map the program input to a set of multiple device templates each comprising one or more logical variables and a set of substitutions for the logical variables which represent solutions to the constraints by substituting a specific part for each of the logical variables.

15. A system as claimed in claim 14, wherein the substitutions from logical variables to specific parts are injective such that distinct logical variables are mapped to distinct parts from the genetic parts database.

16. A system as claimed in claim 13, wherein at least one of the constraints in the program input comprises a compartment that specifies a location of a first subset of the parts within the compartment and a second subset of the parts outside of the compartment.

17. A system as claimed in claim 16, wherein the compiler is arranged to detect cross-talk between parts within a same compartment and resolve the at least one constraint to avoid cross-talk between the parts in the same compartment.

* * * * *